May 24, 1966 E. S. BOERNER Plant Pat. 2,635
ROSE PLANT
Filed April 29, 1965
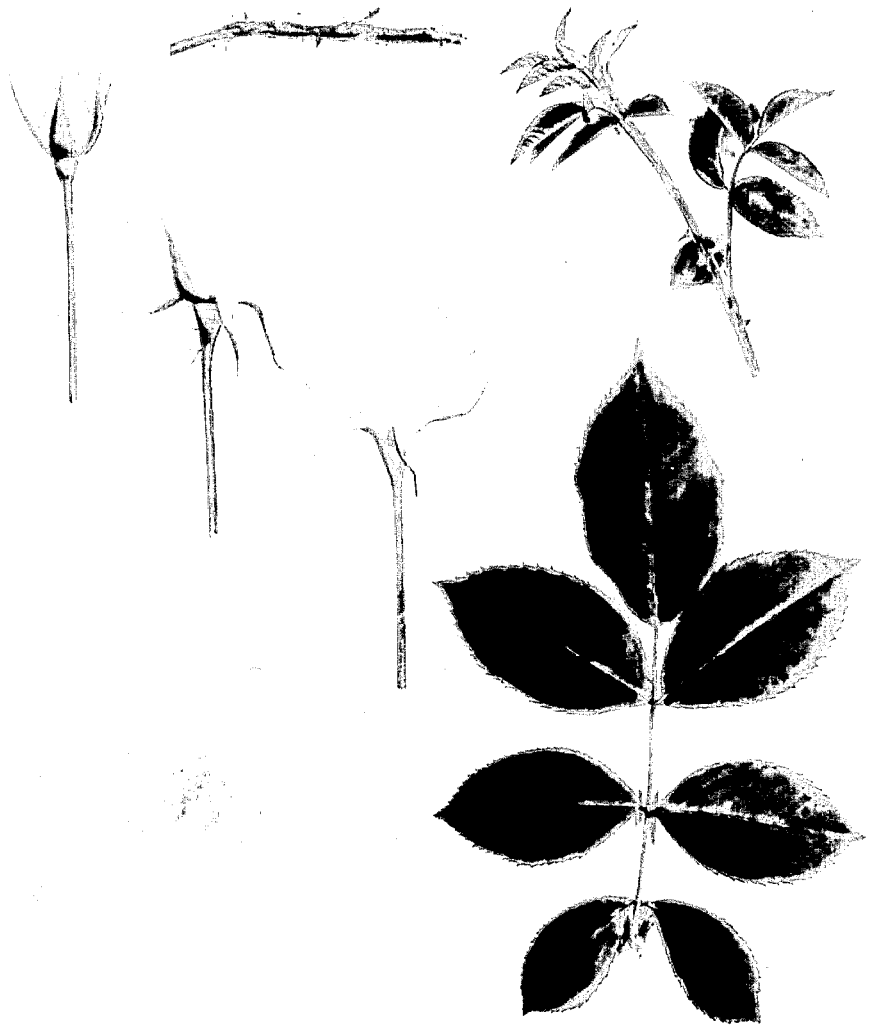
Inventor.
E. S. Boerner
By: Robb & Robb
Attorneys

United States Patent Office

Plant Pat. 2,635
Patented May 24, 1966

2,635
ROSE PLANT

Eugene S. Boerner, Newark, N.Y., assignor to Jackson & Perkins Company, Newark, N.Y., a corporation of New York Filed Apr. 29, 1965, Ser. No. 452,037
1 Claim. (Cl. Plt.—27)

The present invention relates to a new and distinct variety of rose plant of the floribunda class, which was originated by me by crossing an unnamed and unpatented seedling derived from a cross of "Fashion" (Plant Patent No. 789) × an unnamed and unpattented seedling of "Garnette" (unpatented) with the variety "Spartan" (Plant Patent No. 1,357).

The primary objective of this breeding was to produce a new and improved rose variety which bears flowers of the "Garnette" type, with the same stiffness of the flower petals, but the flowers being of a different color. This objective was fully achieved along with other desirable improvements, as evidenced by the following unique combination of characteristics which are outstanding in the new variety and which distinguish it from its parents, as well as from all other varieties of which I am aware:

(1) Good foliage of the "Spartan" type;
(2) A continuous blooming habit;
(3) Long flower stems;
(4) Stiff flower petals like those of "Garnette"; and
(5) A distinctive and attractive general color tonality of the flowers corresponding to Rose Red, overcast with Spinel Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling derived from a cross of "Fashion" × an unnamed seedling of "Garnette."
*Pollen parent.*—"Spartan."
Classification:
*Botanic.*—Floribunda.
*Commercial.*—Floribunda.

*Flower*

(Observations made from specimens grown in greenhouses at Newark, New York, in mid-morning during the early part of October.)

Blooming habit: Recurrent—continuous.
Bud:
*Size.*—Medium.
*Form.*—Ovoid; not affected by wet or hot weather.
*Color.*—When sepals first divide—Rose Red, Plate 12. When petals begin to unfurl—Spinel Pink, Plate 26, very lightly overcast with Rose Red, Plate 12. When half-blown: Inside of petals—Begonia Rose, Plate 1, very lightly overcast with Spinel Pink, Plate 26; reverse of petals—Eosine Pink, Plate 1, very lightly overcast with Spinel Pink, Plate 26.
*Sepals.*—Branched; curl back when petals begin to unfurl. Color: Inside—Pale Olivine Green, Plate 32; outside—Light Elm Green, Plate 17.
*Calyx.*—Color—Light Elm Green, Plate 17. Shape—pear. Size—small. Aspect—smooth. Odor when rubbed—none.
*Peduncle.*—Length—medium. Aspect — smooth. Strength—erect; slender. Color—Light Bice Green, Plate 17.
*Opening.*—Opens up well; is not affected by adverse weather conditions.
Bloom:
*Size.*—Large. Average size when fully expanded—4½ inches.
*Borne.*—Both singly and several together.
*Stems.*—Long; strong.
*Form (when first open).*—Cupped. Permanence—retains its form to the end.
*Petalage.*—Double (full but open center). Number of petals under normal conditions—25.
*Color.*—Center of flower—Rose Red, Plate 12. Outer petals—Spinel Pink, Plate 26, very lightly overcast with Rose Red, Plate 12. Base of petals (aiglet)—Pale Chalcedony Yellow, Plate 17. Inside of petals—Rose Red, Plate 12, overcast with Spinel Pink, Plate 26. Reverse of petals—Spinel Pink, Plate 26, very lightly overcast with Deep Rose Pink, Plate 12, General tonality from a distance—Rose Red, Plate 12, overcast with Spinel Pink, Plate 26.
*Discoloration.*—General tonality at end of first day—Rose Red, Plate 12, overcast with Spinel Pink, Plate 26. Second day—Rose Red, Plate 12, overcast with Spinel Pink, Plate 26. Third day—Spinel Pink, Plate 26, lightly overcast with Rose Red, Plate 12.
Petals:
*Texture.*—Thick and stiff; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long.

*Genital organs*

Stamens, anthers: Medium size; many; regularly arranged around styles. Color—Deep Chrome, Plate 3.
Stamens, filaments (threads): Long. Color—Empire Yellow, Plate 4.
Pollen: Color—Pale Yellow-Orange, Plate 3.
Styles: Bunched; uneven length; medium length; thin.
Stigmas: Color—Pale Yellow-Orange, Plate 30.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Abundant.
*Color.*—New foliage: Upper side—Bordeaux, Plate 12; under side—Bordeaux, Plate 12, with center of leaf and mid-rib Light Hellebore Green, Plate 17. Old foliage: Upper side—Forest Green, Plate 17; under side—Light Bice Green, Plate 17.
*Shape.*—Oval pointed.

*Texture.*—Upper side—leathery and strong like rose "Spartan." Under side—smooth.

*Ribs and veins.*—Ordinary.

*Edge.*—Serrated (saw toothed).

*Serration.*—Both double and single; small.

*Leaf stem.*—Color—Courge Green, Plate 17. Under side—smooth.

*Stipules.*—Medium length; bearded.

Wood:

*New wood.*—Color—Rinemann's Green, Plate 18, lightly overcast with Bordeaux, Plate 12. Bark—smooth.

*Old wood.*—Color—Civette Green, Plate 18. Bark—smooth.

Thorns:

*Thorns.*—Quantity: On main stalks from base—ordinary; on laterals from stalk—ordinary. Form—narrow base; medium length; hooked downward.

Color (when young)—Flesh Color, Plate 14. Position—irregular.

*Prickles.*—Quantity: On main stalks—none; on laterals—none.

*Short needles.*—Quantity: On main stalks—none; on laterals—none.

I claim:

A new and distinct variety of rose plant of the floribunda class, substantially as herein shown and described, characterized particularly as to novelty by the unique combination of good foliage of the "Spartan" type, a continuous blooming habit, long flower stems, stiff flower petals like those of "Garnette," and a distinctive and attractive general color tonality of the flowers corresponding to Rose Red, overcast with Spinel Pink.

No references cited.

ABRAHAM G. STONE, *Primary Examiner.*